(12) United States Patent
Tran

(10) Patent No.: US 6,432,943 B1
(45) Date of Patent: *Aug. 13, 2002

(54) METHOD FOR TREATING SEXUAL DYSFUNCTION

(75) Inventor: Pierre Van Tran, Carmel, IN (US)

(73) Assignee: Eli Lilly and Company, Indianapolis, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1 days.

(21) Appl. No.: 09/162,311

(22) Filed: Sep. 28, 1998

Related U.S. Application Data

(60) Provisional application No. 60/060,415, filed on Sep. 30, 1997.

(51) Int. Cl.[7] ............................................... A61K 31/55
(52) U.S. Cl. ....................................................... 514/220
(58) Field of Search .......................................... 514/220

(56) References Cited

U.S. PATENT DOCUMENTS 5,229,382 A * 7/1993 Chakrabarti et al. ........ 514/220
5,817,657 A   10/1998 Beasley, Jr. et al. ........ 514/220

OTHER PUBLICATIONS

DRUGU abstract AN 88–35458, Petersen, G., 1988.*
DRUGU abstract AN 86–23473, Smith, P.J. et al., 1986.*
D. Baldwin et al.: "Schizophrenia, antipsychotic drugs and sexual function," Prim. Care Psychiatry, vol. 3, No. 3, 1997, pp. 115–123.
D.E. Casey: "Side effects profiles of new antipsychotic agents." J. Clin. Psychiatry, vol. 57, No. suppl. 11, 1996, pp. 40–45.

* cited by examiner

Primary Examiner—Russell Travers
Assistant Examiner—Shengjun Wang
(74) Attorney, Agent, or Firm—Nelsen L. Lentz; Arleen Palmberg

(57) ABSTRACT

The invention provides a method for treating a sexual dysfunction comprising administering an effective amount of 2-methyl-4-(4-methyl-1-piperazinyl)-10H-thieno[2,3-b][1,5]benzodiazepine.

12 Claims, No Drawings

METHOD FOR TREATING SEXUAL DYSFUNCTION

CROSS-REFERENCE

This application claims the benefit of U.S. Provisional Application No. 60/060,415, filed Sep. 30, 1997.

FIELD OF THE INVENTION

This invention provides a method for using 2-methyl-4-(4-methyl-1-piperazinyl)-10H-thieno[2,3-b][1,5]benzodiazepine, for the treatment of sexual dysfunction.

BACKGROUND OF THE INVENTION

During recent years, sexual dysfunction in humans has become recognized as an increasingly important clinical entity. Such recognition is due in no small part to the pioneering work of William H. Masters and Virginia E. Johnson. In their books, *Human Sexual Response,* Little Brown and Company, Boston, 1966, and *Human Sexual Inadequacy,* Little Brown and Company, Boston, 1970, human sexual response is divided into four phases— excitement phase, plateau phase, orgasmic phase and resolution phase. Any disturbance or variation in this pattern is characterized by them (and others) as a sexual dysfunction.

A more recent, and preferable, categorization of human sexual response is that set forth in *Disorders of Sexual Desire,* Helen Singer Kaplan, M.D., Ph.D., Brunner Mazel Book, Inc., New York, N.Y., 1979. Dr. Kaplan utilizes a triphasic concept of human sexuality—desire, excitement and orgasm. In males, the term "libido" has been used previously to describe the pre-excitement phase of sexual response. The excitement phase in both males and females is characterized by reflex vasodilatation of the genital blood vessels, resulting in an erection in males and by heightened coloring of the labia and lubrication in females. Disorders of the male excitement and desire phases are generally classified under the term impotence, inability to attain or maintain an erection, although some authors restrict the term to an erection disability alone. Dysfunction of the female excitement phase, inhibition of lubrication and swelling, is a relatively uncommon clinical syndrome.

Disorders of the orgasm phase in males includes premature or retarded ejaculation, and anorgasm in both males and females.

Sexual dysfunction, a disorder of one or more of the three phases of sexual response, has generally been treated by counseling. Drug treatment of such disorders has been rare. Masters and Johnson do record the treatment of elderly males with androgens, limited success only being attained.

Sexual dysfunction, besides being in part psychogenic in origin, also includes dysfunctions brought about as a direct result of disease (diabetes) or as an indirect result; i.e., drugs used for treating hypertension in males frequently cause impotence. Kaplan, in Table 1, an appendix, lists the effect of drugs on the sexual response. Drugs are classed as sedative-hypnotics, including alcohol and barbiturates, antianxiety drugs, such as valium and librium, narcotics, such as morphine, the various antipsychotic agents, including phenothiazines and haldol, antidepressants, including the tricyclic antidepressants and the MAO inhibitors, stimulants such as cocaine, hallucinogens including LSD, miscellaneous CNS agents, including L-DOPA and parachlorophenylalanine, hormones, antihypertensives, antiadrenergic drugs, anticholinergic drugs, aphrodisiacs, etc. An examination of Table 1 indicates that a great majority of the drugs and drug types have no effect on the desire or excitement phase of the sexual response. A number of the drugs or drug types, however, are shown to cause impotence and thus may be a cause of sexual dysfunction. Cocaine and the aphrodisiacs alone seem to affect impotence in a positive manner. Many of the drugs in the table are said to cause impotence. It might also be noted that in the centrally acting antihypertensives, impotence is a major problem. L-DOPA, while having no affect on the excitement or orgasmic phases, is reported to increase desire in the elderly male patients afflicted with Parkinsonism. p-Chlorophenylalanine, an inhibitor of serotonin synthesis, is an aphrodisiac in rats but apparently has no effect on humans as well as will be set forth below.

It should also be noted that many of the drugs treat symptoms associated with sexual dysfunction and not the organic cause of the disease itself. For example, Kaplan reports a high degree of anxiety associated with sexual dysfunction in both males and females. An antianxiety drug would, therefore, be expected to have some positive effect in the treatment of such patients merely by alleviating the anxiety.

Extensive research has been conducted for a number of years directed toward the development of compounds for treating sexual dysfunction in mammals. For example, bromocriptine, yohimbine, buproen, naltrixine, methysergide, susperene and gonadotropin releasing hormone have all been evaluated for treating sexual dysfunction. However, to date such compounds have proven unsatisfactory for a variety of reasons including insufficient efficacy or presence of undesirable side effects.

It is known that the compound 2-methyl-4-(4-methyl-1-piperazinyl)-10H-thieno[2,3-b][1,5]benzodiazepine can provide antipsychotic activity and is less likely to induce extrapyramidal symptoms. However, Applicant has discovered that surprisingly 2-methyl-4-(4-methyl-1-piperazinyl)-10H-thieno[2,3-b][1,5]benzodiazepine can be useful for treating sexual dysfunction. The compound 2-methyl-4-(4-methyl-1-piperazinyl)-10H-thieno[2,3-b][1,5]benzodiazepine is known and described in U.S. Pat. No. 5,229,382, herein incorporated by reference in its entirety.

SUMMARY OF THE INVENTION

The presently claimed invention provides a method for treating sexual dysfunction comprising administering an effective amount of 2-methyl-4-(4-methyl-1-piperazinyl)-10H-thieno[2,3-b][1,5]benzodiazepine or a pharmaceutically acceptable salt thereof to a patient in need of such treatment.

DETAILED DESCRIPTION OF THE INVENTION

The 2-methyl-4-(4-methyl-1-piperazinyl)-10H-thieno[2,3-b][1,5]benzodiazepine compound is of the formula

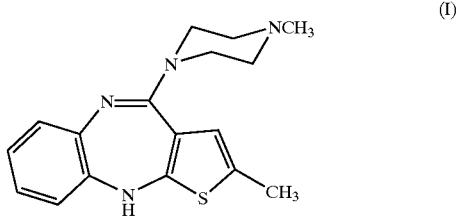

(I)

or an acid addition salt thereof. The free base of formula (I) is 2-methyl-4-(4-methyl-1-piperazinyl)-10H-thieno[2,3-b][1,5]benzodiazepine.

The substantially pure crystalline anhydrous Form I 2-methyl-4-(4-methyl-1-piperazinyl)-10H-thieno[2,3-b][1,5]benzodiazepine (Form I) has a typical X-ray powder diffraction pattern substantially as follows, using a Sieman's D5000 diffractometer equipped with a copper radiation source, wherein d represents the interplaner spacing:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

Form II 2-methyl-4-(4-methyl-1-piperazinyl)-10H-thieno[2,3-b][1,5]benzodiazepine (Form II) has a typical X-ray powder diffraction pattern substantially as follows, using a Sieman's D5000 diffractometer equipped with a copper radiation source, wherein d represents the interplaner spacing:

| d | $I/I_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.595 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns set forth herein were obtained with a copper K of wavelength=1.541A. The interplanar spacings in the column marked "d" are in Angstroms. The typical relative intensities are in the column marked "$I/I_1$". The detector was a Kevex silicon lithium solid state detector.

As used herein "substantially pure" shall refer to anhydrous Form I associated with <5% Form II; and most preferably it shall refer to <2% Form II. It is further preferred that "substantially pure" shall refer to <0.5% non-Form I polymorph.

As used herein "substantially pure" shall refer to anhydrous Form I associated with about <5% Form II; and most preferably it shall refer to about <2% Form II. It is further preferred that "substantially pure" shall refer to <0.5% related substances. When the Form I polymorph is formulated as a pharmaceutical composition, "substantially pure" shall preferably refer to about <15% Form II polymorph; more preferably, the term shall refer to about <10% Form II polymorph when the Form I polymorph is formulated as a pharmaceutical, and it is especially preferred that the term shall refer to about <5% Form II polymorph when the substantially pure substance is formulated.

As used herein, the term "2-methyl-4-(4-methyl-1-piperazinyl)-10H-thieno[2,3-b][1,5]benzodiazepine" refers to a technical grade of 2-methyl-4-(4-methyl-1-piperazinyl)-10H-thieno[2,3-b][1,5]benzodiazepine when no specific solvate or polymorph is named. Typically, the technical grade 2-methyl-4-(4-methyl-1-piperazinyl)-10H-thieno[2,3-b][1,5]benzodiazepine contains less than about 5% undesired related substances and may be a mixed polymorph. Such technical grade 2-methyl-4-(4-methyl-1-piperazinyl)-10H-thieno[2,3-b][1,5] benzodiazepine may contain less than about 1% undesired related substances.

The term "crude" refers to a form of 2-methyl-4-(4-methyl-1-piperazinyl)-10H-thieno[2,3-b][1,5]benzodiazepine typically associated with undesired polymorph and/or greater than about 5% undesired related substances. Such crude grade 2-methyl-4-(4-methyl-1-piperazinyl)-10H-thieno[2,3-b][1,5]benzodiazepine may contain less than about 1% undesired related substances.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

The term "sexual dysfunction" as used herein means any disturbance related to sexual desire, excitement or orgasm in mammals. Included are disorders related to the erectile response in male mammals and the sexual desire and sexual (both arousal and orgasmic) reflexes in male or female mammals. Such disorders include those that are naturally occurring, drug-induced or disease related. Accordingly, the compounds of formula I can be used to treat decreased libido, erectile dysfunction, retarded ejaculation and anorgasmy. The compounds can, further, be also used to increase sexual desire in mammals of both sexes.

The results of pharmacological studies show that 2-methyl-4-(4-methyl-1-piperazinyl)-10H-thieno[2,3-b][1,5]benzodiazepine has muscarinic cholinergic receptor activity. The compound is active at the dopamine D-1 and D-2 receptors as indicated by an IC50 of less than 1 uM in the 3H-SCH233390 (Billard, et al. Life Sciences 35:1885 (1984)) and the 3H spiperone (Seeman, et al., Nature 216:717 (1976)) binding assays respectively. Further, the anhydrous Form I compound is active at the 5-HT-2 receptor and 5-HT1C receptor. The complex pharmacological profile of the compound provides a medicament which can be useful for the treatment of sexual dysfunction.

In vivo animal and clinical observations support that 2-methyl-4-(4-methyl-1-piperazinyl)-10H-thieno[2,3-b][1,5]benzodiazepine has a complex muscarinic receptor subtype profile. For example, rats exposed to an overdose of the compound surprisingly exhibited significant salivation. Further, clinical subjects experienced pupilary constriction rather than the expected pupilary dialation.

The usefulness of the compound for treating sexual dysfunction can be supported by the following studies as described.

I. The ability of the Compounds of the Present Invention to Affect Sexual Behavior in Male Animals was Established by the Following Experiments Adult male rats of the Sprague-Dawley strain are used in these studies. The sexual behavior evaluations are conducted at 2-week intervals beginning at 6 months of age and ending at 12 months of age. During the initial screening process, the male rats of various levels of sexual performance are selected for compound testing. These performance levels included male rats that display no mounting behavior (Non-Maters); male rats that are able to mount but were unable to ejaculate during the test period (Non-Ejaculators); and male rats that are able to ejaculate during the test period. Prior to treatment with a drug solution, each male rat requires at least two consecutive vehicle tests with similar sexual performance. Following each compound testing, additional vehicle tests are performed. In an effort to eliminate behavioral responses with compound treatment that may be due to spontaneous changes in mating performance, a criterion of reversibility of behavioral response with subsequent vehicle treatment is employed. Thus, a valid behavioral response to a drug treatment is arbitrarily set as a response that either did not change from the prior control response or is reversed in the subsequent control test with vehicle.

The mating tests are performed during the dark phase of the lighting cycle using red light illumination. Each behavioral test is initiated with the introduction of a receptive female rat into the arena and is terminated either 30 minutes later or immediately following the first postejaculatory mount. The indices of mating performance that are evaluated for the rats capable of ejaculation included mount latency (the time interval from the introduction of the female rat to the first mount); intromission latency (the time interval from the introduction of the female rat to the first intromission); ejaculatory latency (the time interval from intromission to ejaculation); postejaculatory interval (the time from ejaculation to the next mount); mount frequency (the total number of mounts with or without intromission prior to ejaculation); intromission frequency (the number of mounts with intromission prior to ejaculation); intromission efficiency (the intromission frequency divided by the mount frequency); copulatory rate (the number of mounts per minute); copulatory frequency (the number of mounts prior to ejaculation); and copulatory efficiency (the number of mounts with intromission divided by the total number of mounts).

Each male rat is given a solution containing either the vehicle alone in water or 2-methyl-4-(4-methyl-1-piperazinyl)-10H-thieno[2,3-b][1,5]benzodiazepine, in the same vehicle. Vehicle is made of 1 mM (millimolar) acetic acid and 1 mM ascorbic acid.

II. The Ability of the Compounds of the Present Invention to Affect Sexual Behavior in Female Animals was Established by the Following Experiment The effects of 2-methyl-4-(4-methyl-1-piperazinyl)-10H-thieno[2,3-b][1,5]benzodiazepine on sexual behavior of female mammals is evaluated in ovariectomized, estrogen-treated rats.

The change in the lordosis-to-mount ratio is measured (increase in presenting by the female for mounting by a male per mount). The protocol of Foreman and Moss, *Physiology and Behavior,* 22, 283 (1979), is used.

III. Clinical Observations

A double-blind multicenter clinical trial is designed to assess the safety and efficacy of 2-methyl-4-(4-methyl-1-piperazinyl)-10H-thieno[2,3-b][1,5]benzodiazepine in patients with a sexual dysfunction. Five to fifty patients are selected for the clinical study. The patients suffer from sexual dysfunction. The study has a placebo control group, i.e., the patients are divided into two groups, one of which receives a compound of formula 1 as the active agent and the other receives a placebo. Patients in the test group receive between 0.25 and 50 mg of the drug per day by the oral route. They continue this therapy for 3–12 months. Accurate records are kept as to the symptoms in both groups and at the end of the study these results are compared. The results are compared both between members of each group and also the results for each patient are compared to the status reported for each patient before the study began.

The compound 2-methyl-4-(4-methyl-1-piperazinyl)-10H-thieno[2,3-b][1,5]benzodiazepine can be used for the methods of this invention, both in its free base and acid addition salt forms. The acid addition salts are preferably the pharmaceutically acceptable, non-toxic addition salts with suitable acids, such as those of inorganic acids, for example hydrochloric, hydrobromic, nitric, sulfuric or phosphoric acids, or of organic acids, such as organic carboxylic acids, for example glycollic, maleic, hydroxymaleic, fumaric, malic, tartaric, citric or lactic acid, or organic sulfonic acids for example methane sulfonic, ethane sulfonic, 2-hydroxyethane sulfonic, toluene-p-sulfonic or naphthalene-2-sulfonic acid.

The compound 2-methyl-4-(4-methyl-1-piperazinyl)-10H-thieno[2,3-b][1,5]benzodiazepine can be prepared using a process which comprises (a) reacting N-methylpiperazine with a compound of the formula

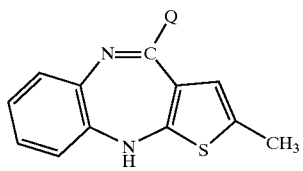

(II)

in which Q is a radical capable of being split off, or (b) ring-closing a compound of the formula

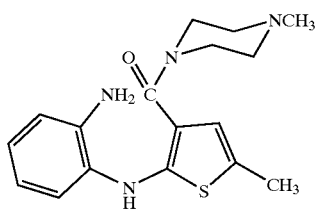
(III)

Appropriate reaction conditions and suitable values of Q can readily be chosen for these processes.

In reaction (a) the radical Q can, for example, be an amino group or a mono- or dialkyl-substituted amino group (each alkyl substituent suitably containing 1 to 4 carbon atoms), hydroxyl, thiol, or an alkoxy, alkylthio or alkylsulfonyl group suitably containing 1 to 4 carbon atoms, for example a methoxy or methylthio group, or a halogen atom, especially a chlorine atom. Preferably, Q is amino (—NH$_2$), hydroxyl or thiol, and amino is most preferred. The reaction is preferably carried out at a temperature of from 50° C. to 200° C.

When Q is amino, the intermediate of formula (II) may also exist in the imino form:

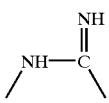

and when Q is hydroxyl or thiol, the intermediates of formula (II) may exist in their amide and thioamide forms:

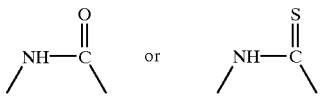

The amidine of formula (II) (Q is —NH$_2$), can be in salt form, for example a salt of a mineral acid such as the hydrochloride, and can be reacted with N-methylpiperazine in an organic solvent such as anisole, toluene, dimethylformamide or dimethylsulfoxide, preferably at a temperature range of 100 to 150° C.

The amidine is prepared by condensing a thiophene compound of formula

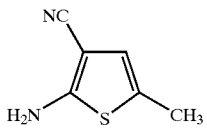

with an ortho-halonitrobenzene, in the presence of a base, for example sodium hydride, in a solvent such as tetrahydrofuran or n-butyl lithium in tetrahydrofuran, or potassium carbonate or lithium hydroxide in dimethylsulfoxide or aqueous sodium hydroxide in dimethylsulfoxide, or with a tetraalkyl-ammonium salt in a two-phase system, to form a nitronitrile of formula:

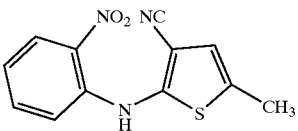
(IIa)

which can be simultaneously reduced and ring-closed to the amidine of formula (II) employing, for example, stannous chloride and hydrogen chloride in aqueous ethanol or, alternatively by reduction with hydrogen and palladium/carbon or ammonium polysulfide followed by acid-catalyzed ring closure. The intermediate of formula (IIa) may be isolated using ammonium chloride (NH$_4$Cl) or ammonium acetate (NH$_4$OAc).

When Q is hydroxyl, reaction (a) is preferably carried out in the presence of titanium tetrachloride which has the ability to react with the N-methylpiperazine to form a metal amine complex. Other metal chlorides such as those of zirconium, hafnium or vanadium may also be employed. The reaction can be carried out in the presence of an acid binding agent such as a tertiary amine, for example, triethylamine.

Alternatively, the reaction can be carried out using excess of N-methylpiperazine to act as an acid-binding agent. A suitable organic solvent such as toluene or chlorobenzene can be used as a reaction medium, although the use of anisole is particularly desirable, at least as a co-solvent, in view of its ability to form a soluble complex with TiCl$_4$.

If desired, elevated temperatures, for example up to 200° C., can be used to hasten the reaction and a preferred temperature range for carrying out the reaction is from 80° C. to 120° C.

The intermediate amide of formula (II) (Q is —OH) can be prepared from the corresponding amidine (Q is —NH$_2$) by alkaline hydrolysis, or can be derived from compounds of formula

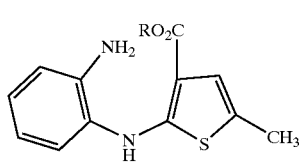
(IV)

in which R is an ester group, preferably C$_{1-4}$ alkyl, by ring closure employing, for example, sodium methylsulfinyl methanide in a suitable solvent such as dimethylsulfoxide. Alternatively, the amide can be prepared by ring closure of an amino-acid, employing for example dicyclohexylcarbodiimide (DCC) in a suitable solvent such as tetrahydrofuran. The amino-acid can be obtained for example from the above esters by basic hydrolysis using for example sodium hydroxide in ethanol.

Thioamides of formula (II) (Q is —SH), iminothioethers, iminoethers or iminohalides, or other derivatives containing active Q radicals as specified above, tend to be more reactive towards N-methylpiperazine and can usually be reacted without the necessity for the presence of TiCl$_4$, but otherwise employing the same conditions of temperature and solvent.

The thioamide of formula (II) (Q is —SH) can be prepared by treating a solution of the corresponding amide in an anhydrous basic solvent, such as pyridine, with phosphorous pentasulfide. Similarly, the amide can be converted to the iminothioether, iminoether or iminohalide, or other derivatives containing active Q radicals, by treatment with conventional reagents such as for example in the case of the iminochloride, phosphorous pentachloride.

The intermediate compounds of formula (II) in which Q is a radical capable of being split off, particularly those in which Q is —NH₂, —OH or —SH and when Q is —NH₂ salts thereof, are novel compounds, and form a further aspect of the present invention.

With regard to reaction (b) above, the compound of formula (III) may be ring-closed by employing, for example, titanium tetrachloride as catalyst and anisole as solvent, and the reaction is preferably carried out at a temperature of 100° C. to 250° C., for example from 150° C. to 200° C.

The intermediate compound of formula (III) is preferably prepared in situ without isolation by reacting a compound of formula

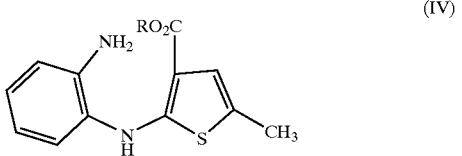

(IV)

in which R is an ester group, preferably $C_{1-4}$ alkyl, with N-methylpiperazine, by heating to a temperature of between 30° C. and 120° C., for example about 100° C., in a suitable solvent such as for example anisole, and employing $TiCl_4$ as catalyst.

The compound of formula (IV) can be prepared from the corresponding nitro compound of formula

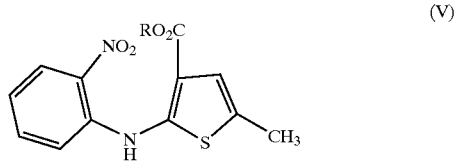

(V)

Such compounds of formula (V) in which R is an ester group, such as for example $C_{1-4}$ alkyl, are novel and form a further aspect of the invention.

If convenient this nitro compound can be converted to the amine of formula (IV) without isolation, before reaction with N-methylpiperazine. Intermediate compounds of formula (V) can be made by condensation of a thiophene of formula

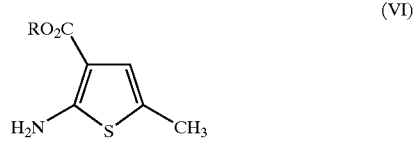

(VI)

with an ortho-halonitrobenzene, preferably ortho fluoro- or chloro-nitrobenzene, in the presence of a base, for example, (a) sodium hydride in a solvent such as for example tetrahydrofuran and at a temperature of from –20° C. to 30° C., or (b) anhydrous potassium carbonate or lithium hydroxide in a solvent such as dimethylsulfoxide at a temperature of from 90° C. to 120° C. The compound of formula (V) is converted to that of formula (IV) by reduction, for example catalytically, employing hydrogen and palladium/carbon, or chemically, employing stannous chloride and hydrogen chloride in aqueous ethanol, or ammonium polysulfide, or zinc in aqueous ammonium chloride.

It will be appreciated that the compound of formula (I) may be isolated per se or may be converted to an acid addition salt using conventional methods.

The compound has an $IC_{50}$ of less than 1 mM in the ³H-QNB binding assay described by Yamamura, HI and Snyder, SH in Proc.Nat.Acad.Sci. USA 71 1725 (1974) indicating that it has muscarinic-cholinergic activity.

The 2-methyl-4-(4-methyl-1-piperazinyl)-10H-thieno-[2,3-b][1,5]benzodiazepine compound is effective over a wide dosage range, the actual dose administered being dependent on the condition being treated. For example, in the treatment of adult humans, dosages of from about 0.25 to 50 mg, preferably from 1 to 30 mg, and most preferably 1 to 20 mg per day may be used. A once a day dosage is normally sufficient, although divided doses may be administered. For treatment of cognitive dysfunction, a dose range of from 1 to 30 mg, preferably 1 to 20 mg per day is suitable. Radiolabelled 2-methyl-4-(4-methyl-1-piperazinyl)-10H-thieno-[2,3-b][1,5]benzodiazepine, can be detected in the saliva and thus the compound can potentially be monitored in patients to assess compliance.

A preferred formulation of the invention is a solid oral formulation comprising from about 1 to about 20 mg or 1 to 10 mg of active anhydrous Form I 2-methyl-4-(4-methyl-1-piperazinyl)-10H-thieno[2,3-b][1,5]benzodiazepine as an effective amount of the active ingredient.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

The 2-methyl-4-(4-methyl-1-piperazinyl)-10H-thieno-[2,3-b][1,5]benzodiazepine compound will normally be administered orally or by injection and, for this purpose, it is usually employed in the form of a pharmaceutical composition.

Accordingly, pharmaceutical compositions comprising 2-methyl-4-(4-methyl-1-piperazinyl)-10H-thieno[2,3-b][1,5]benzodiazepine, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient. For example, one such preferred quick release formulation is described in U.S. Pat. Nos. 5,079,018, 5,039,540, 4,305,502, 4,758,598, and 4,371,516, hereby incorporated by reference. Such formulation most preferably comprises 2-methyl-4-(4-methyl-1- piperazinyl)-10H-thieno[2,3-b][1,5]benzodiazepine, water, hydrolyzed gelatin, and mannitol.

Depending on the method of administration, the compositions for the treatment of central nervous system conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 0.25 to 100 mg, more usually 1 to 30 mg, of the active ingredient. When a sustained release formulation is desired, the unit dosage form may contain from 0.25 to 200 mg of the active ingredient. A preferred formulation of the invention is a capsule or tablet comprising 0.25 to 75 mg or 1 to 30 mg of active ingredient together with a pharmaceutically acceptable carrier therefor. A further preferred formulation is an injection which in unit dosage form comprises 0.25 to 30 mg or 1 to 30 mg of active ingredient together with a pharmaceutically acceptable diluent therefor.

The materials for the present invention can be purchased or prepared by a variety of procedures well known to those of ordinary skill in the art. The 2-methyl-4-(4-methyl-1-piperazinyl)-10H-thieno[2,3-b][1,5]benzodiazepine compound can be prepared as described by Chakrabarti in U.S. Pat. No. 5,229,382 ('382), herein incorporated by reference in its entirety. It is most desirable to prepare a rapidly dissolving formulation comprising substantially pure crystalline Form I 2-methyl-4-(4-methyl-1-piperazinyl)-10H-thieno[2,3-b][1,5]benzodiazepine. Such substantially pure crystalline Form I 2-methyl-4-(4-methyl-1-piperazinyl)-10H-thieno[2,3-b][1,5]benzodiazepine may be prepared using the techniques described herein by the Preparation section herein infra.

As used herein mixing steps may be accomplished using common agitation methods such as stirring, shaking, and the like. As used herein the phrase "producing crystalline product from the mixture" shall refer to crystallization from the stated mixture of compound and solvent. Further, the artisan recognizes that crystallization processes may include seeding, chilling, scratching the glass of the reaction vessel, and other such common techniques.

Compound characterization methods include, for example, x-ray powder pattern analysis, thermogravimetric analysis (TGA), differential scanning calorimetery (DSC), titrametric analysis for water, and H$^1$-NMR analysis for solvent content.

The following examples are provided for purposes of illustration and are not to be construed as limiting the scope of the claimed invention.

Preparation 1

Crystalline Form II 2-methyl-4-(4-methyl-1-piperazinyl)-10H-thieno[2,3-b][1,5]benzodiazepine A 10 gram sample of crude 2-methyl-4-(4-methyl-1-piperazinyl)-10H-thieno[2,3-b][1,5]benzodiazepine was suspended in methylene chloride (100)gm and stirred at ambient temperature (20–25° C.) for a period of 1 hour. The slurry was vacuum filtered and the filtrate was recovered. The stirred filtrate was chilled to 0–5° C. in an ice bath and the solvent was slowly evaporated under a stream of nitrogen to a thick paste. Approximately ¾ of the solvent was removed by evaporation. A quantity of prechilled methylene chloride (30 gm, 0–5° C.) was mixed into the thick paste. The resulting slurry was vacuum filtered and allowed to air dry on the filter. The isolated solid was further dried in a vacuum oven at 50° C. for a period of 30 minutes. Isolated: 4.8 gm. X-ray powder characterization: Form II+CH$_2$Cl$_2$ Solvate.

The isolated solid was redried in a vacuum oven at 50° C. under a stream of nitrogen for a period of 30 hours. Isolated: 4.5 gm X-ray powder characterization: Form II. (described supra.)

Preparation 2

Form I 2-methyl-4-(4-methyl-1-piperazinyl)-10H-thieno[2,3-b][1,5]benzodiazepine

A sample of ethyl acetate which was saturated with technical grade 2-methyl-4-(4-methyl-1-piperazinyl)-10H-thieno[2,3-b][1,5]benzodiazepine was contacted with Form II 2-methyl-4-(4-methyl-1-piperazinyl)-10H-thieno[2,3-b][1,5]benzodiazepine (0.3 g), a seed of anhydrous Form I 2-methyl-4-(4-methyl-1-piperazinyl)-10H-thieno[2,3-b][1,5]benzodiazepine and stirred at about 25° C. for about 5 hours. The reaction product was isolated by vacuum filtration and dried under ambient conditions. Yield: 0.25 g. X-ray powder analysis indicated that the product was anhydrous Form I 2-methyl-4-(4-methyl-1-piperazinyl)-10H-thieno[2,3-b][1,5]benzodiazepine.

Preparation 3

Technical Grade 2-methyl-4-(4-methyl-1-piperazinyl)-10H-thieno[2,3-b][1,5]benzodiazepine

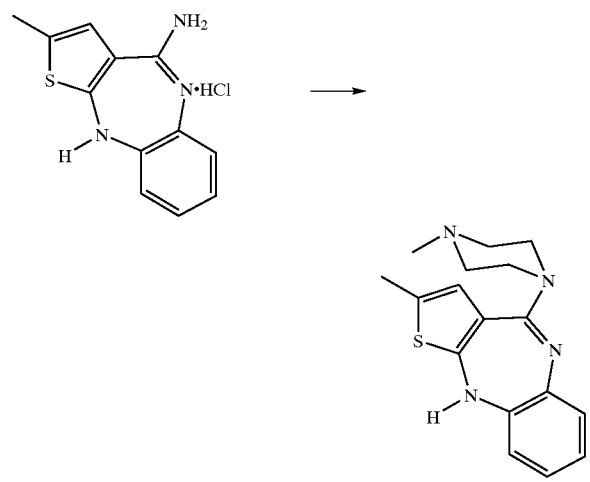

Intermediate 1

In a suitable three neck flask the following was added:
Dimethylsulfoxide (analytical): 6 volumes
Intermediate 1: 75 g
N-Methylpiperazine (reagent): 6 equivalents
Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained throughout the duration of the reaction. The reactions were followed by HPLC until ≦5% of the intermediate 1 was left unreacted. After the reaction was complete, the mixture was allowed to cool slowly to 20° C. (about 2 hours). Each reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical 2-methyl-4-(4-methyl-1-piperazinyl)-10H-thieno[2,3-b][1,5]benzodiazepine.

Yield: 76.7%; Potency: 98.1%

The procedure of Preparation 3 was repeated substantially as described above and provided a yield of 81% with a potency of 101.1%.

Preparation 4

Technical Grade 2-methyl-4-(4-methyl-1-piperazinyl)-10H-thieno[2,3-b][1,5]benzodiazepine Intermediate 1 (supra) was suspended in DMSO (3.2 vol.) and toluene (4.5 vol.). A portion (Å 0.65 vol.) of the solvent was removed by distillation at 120–125° C. The mixture was cooled to 110° C., N-methylpiperazine(NMP, 4.2 equiv.) was added and the mixture heated back to reflux (120–125° C.). Another portion (Å 1 vol.) of the solvent was removed by distillation to dry the reaction mixture. A vigorous reflux was desired to drive the reaction to completion (about 7 hours.) by removing ammonia from the reaction. The product was isolated by the slow addition of water (12.75 vol.) to the cooled (10° C.) reaction solution. The product was collected by filtration and washed with chilled water (2 vol.). The crude 2-methyl-4-(4-methyl-1-piperazinyl)-10H-thieno[2,3-b][1,5]benzodiazepine was dried in vacuo at 60° C. The product was recrystallized from hot toluene (5 vol.) to give a technical grade 2-methyl-4-(4-methyl-1-piperazinyl)-10H-thieno[2,3-b][1,5]benzodiazepine. After drying in vacuo at 50° C., the technical grade 2-methyl-4-(4-methyl-1-piperazinyl)-10H-thieno[2,3-b][1,5]benzodiazepine was recrystallized again from ethyl acetate (10 vol.)/toluene (0.62 vol.)/methanol (3.1 vol.)to give 2-methyl-4-(4-methyl-1-piperazinyl)-10H-thieno[2,3-b][1,5]benzodiazepine as a methanol solvate. The methanol solvate upon drying at >50° C. was converted to an anhydrous technical grade 2-methyl-4-(4-methyl-1-piperazinyl)-10H-thieno[2,3-b][1,5]benzodiazepine.

Preparation 5

Form I from Acetone

A 3.0 g sample of technical grade 2-methyl-4-(4-methyl-1-piperazinyl)-10H-thieno[2,3-b][1,5]benzodiazepine was suspended in acetone (30 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 0.8 g.

Preparation 6

Form I Using Tetrahydrofuran

An 8.0 g sample of technical grade 2-methyl-4-(4-methyl-1-piperazinyl)-10H-thieno[2,3-b][1,5]benzodiazepine was suspended in tetrahydrofuran (25 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 1.3 g.

Preparation 7

Form I Using Ethyl Acetate

A 270 g sample of technical grade 2-methyl-4-(4-methyl-1-piperazinyl)-10H-thieno[2,3-b][1,5]benzodiazepine was suspended in ethyl acetate (2.7 L). The mixture was heated to about 76° C. and maintained at about 76° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 197 g.

Preparation 8

Form I from t-butanol

A 1.0 g sample of technical grade 2-methyl-4-(4-methyl-1-piperazinyl)-10H-thieno[2,3-b][1,5]benzodiazepine was suspended in tert-butanol (30 g). The stirred mixture was heated to about 60° C. and maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 0.3 g.

Preparation 9

Form I from Slurry Conversion of Form II in Toluene

A 0.5 g sample of technical grade 2-methyl-4-(4-methyl-1-piperazinyl)-10H-thieno[2,3-b][1,5]benzodiazepine and a 0.5 g sample of Form II 2-methyl-4-(4-methyl-1-piperazinyl)-10H-thieno[2,3-b][1,5]benzodiazepine were suspended in toluene (5 ml), presaturated with 2-methyl-4-(4-methyl-1-piperazinyl)-10H-thieno[2,3-b][1,5]benzodiazepine. The mixture was stirred in a sealed vial at about ambient temperature for about 22 hours. The resulting product was isolated using vacuum filtration and dried under vacuum at about 45° C. The product was identified as Form I 2-methyl-4-(4-methyl-1-piperazinyl)-10H-thieno[2,3-b][1,5]benzodiazepine using x-ray powder analysis.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the 2-methyl-4-(4-methyl-1-piperazinyl)-10H-thieno[2,3-b][1,5]benzodiazepine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

EXAMPLE 2

The process substantially as described above in Example 1 was repeated using the following ingredients to provide pharmaceutically elegant tablet formulations containing 1, 2.5, 5, 7.5, and 10 mg 2-methyl-4-(4-methyl-1-piperazinyl)-10H-thieno[2,3-b][1,5]benzodiazepine, respectively, per tablet:

1 mg 2-methyl-4-(4-methyl-1-piperazinyl)-10H-thieno[2,3-b][1,5]benzodiazepine per tablet

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 1.0 |
| Other Ingredients | |
| Lactose | 67.43 |
| Hydroxypropyl Cellulose | 3.40 |
| Crospovidone | 4.25 |
| Microcrystalline Cellulose | 8.50 |
| Magnesium Stearate | 0.42 |
| Subcoating | |
| Hydroxypropyl Methylcellulose Coating | 1.70 |
| Color Mixture White Polishing | 3.47 |
| Carnauba Wax Imprinting | trace |
| Edible Blue Ink | trace |

2-methyl-4-(4-methyl-1-piperazinyl)-10H-thieno[2,3-b][1,5]benzodiazepine 2.5 mg Tablets

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 2.5 |
| Other Ingredients | |
| Lactose | 102.15 |
| Hydroxypropyl Cellulose | 5.20 |
| Crospovidone | 6.50 |
| Microcrystalline Cellulose | 13.00 |
| Magnesium Stearate | 0.65 |
| Subcoating | |
| Hydroxypropyl Methylcellulose Coating | 2.60 |
| Color Mixture White Polishing | 5.30 |
| Carnauba Wax Imprinting | trace |
| Edible Blue Ink | trace |

2-methyl-4-(4-methyl-1-piperazinyl)-10H-thieno[2,3-b][1,5]benzodiazepine 5.0 mg Tablets

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 5.00 |
| Other Ingredients | |
| Lactose | 156.00 |
| Hydroxypropyl Cellulose | 8.00 |
| Crospovidone | 10.00 |
| Microcrystalline Cellulose | 20.00 |
| Magnesium Stearate | 1.00 |
| Subcoating | |
| Hydroxypropyl Methylcellulose Coating | 4.00 |
| Color Mixture White Polishing | 8.16 |
| Carnauba Wax Imprinting | trace |
| Edible Blue Ink | trace |

2-methyl-4-(4-methyl-1-piperazinyl)-10H-thieno[2,
3-b][1,5]benzodiazepine 7.5 mg Tablets

| Names of Ingredients | Quantity (mg/tablet) |
|---|---|
| Active Ingredient | |
| 2-methyl-4-(4-methyl-1-piperazinyl)-10H-thieno[2,3-b] [1,5]benzodiazepine | 7.50 |
| Other Ingredients | |
| Lactose | 234.00 |
| Hydroxypropyl Cellulose | 12.00 |
| Crospovidone | 15.00 |
| Microcrystalline Cellulose | 30.00 |
| Magnesium Stearate | 1.50 |
| Subcoating | |
| Hydroxypropyl Methylcellulose Coating | 6.00 |
| Color Mixture White Polishing | 12.24 |
| Carnauba Wax Imprinting | trace |
| Edible Blue Ink | trace |

2-methyl-4-(4-methyl-1-piperazinyl)-10H-thieno[2,
3-b][1,5]benzodiazepine 10.0 mg Tablets

| Names of Ingredients | Quantity (mg/tablet) |
|---|---|
| Active Ingredient | |
| 2-methyl-4-(4-methyl-1-piperazinyl)-10H-thieno[2,3-b] [1,5]benzodiazepine | 10.00 |
| Other Ingredients | |
| Lactose | 312.00 |
| Hydroxypropyl Cellulose | 16.00 |
| Crospovidone | 20.00 |
| Microcrystalline Cellulose | 40.00 |
| Magnesium Stearate | 2.00 |
| Subcoating | |
| Hydroxypropyl Methylcellulose Coating | 8.00 |
| Color Mixture White Polishing | 16.32 |
| Carnauba Wax Imprinting | trace |
| Edible Blue Ink | trace |

EXAMPLE 4

Pulvule Formulation

A pulvule formulation is prepared by blending the active with silicone starch, and filling it into hard gelatin capsules.

| | Per 300 mg capsule |
|---|---|
| Compound of the invention | 30.0 mg |
| Silicone | 2.9 mg |
| Starch flowable | 267.1 mg |

EXAMPLE 5

Tablet Formulation

A tablet formulation is made by granulating the active with appropriate diluent, lubricant, disintegrant and binder and compressing

| | |
|---|---|
| Compound of the invention | 10.0 mg |
| Magnesium stearate | 0.0 mg |
| Microcrystalline cellulose | 75.0 mg |
| Povidone | 15.0 mg |
| Starch, directly compressible | 204.1 mg |

EXAMPLE 6

Aqueous Injection Formulation

An aqueous injection of active is prepared as a freeze-dried plug, for reconstitution in a suitable, sterile diluent before use (to a total volume of 10 ml).

Compound of the invention is contacted with Mannitol N Hydrochloric acid and/or N sodium hydroxide to adjust pH to 5–5.5.

| | |
|---|---|
| Compound of the invention | 20.0 mg |
| Mannitol | 20.0 mg |
| N Hydrochloric acid and/or N sodium hydroxide to adjust pH to 5–5.5. | |

EXAMPLE 7

Controlled Release IM Formulation

A controlled release injection for intramuscular injection is formed from a sterile suspension of micronised active in an oleaginous vehicle.

| | |
|---|---|
| Compound of the invention | 50.0 mg |
| Aluminum stearate | 0.04 mg |
| Sesame oil | 2 ml |

EXAMPLE 8

Capsule Formulation

A formulation is prepared by blending the active with silicone starch and starch, and filling it into hard gelatin capsules.

|  | Per 300 mg capsule |
| --- | --- |
| Compound of the invention | 2.5 mg |
| Starch flowable with 0.96% silicone 220 | 222.5 mg |
| Starch flowable | 75.0 mg |

EXAMPLE 9

2-methyl-4-(4-methyl-1-piperazinyl)-10H-thieno[2,3-b][1,5]benzodiazepine Granules The granules were produced by blending the mannitol and Hydroxymethyl propyl cellulose in a high shear mixer; granulating with the aqueous suspension of 2-methyl-4-(4-methyl-1-piperazinyl)-10H-thieno[2,3-b][1,5]benzodiazepine and polysorbate 20; wet sized and subsequently dried in a fluid bed dryer. These are dry sized and reblended prior to packaging.

| INGREDIENT | MG/SACHET |
| --- | --- |
| 1a. 250 mg Sachets | |
| Active 2-methyl-4-(4-methyl-1-piperazinyl)-10H-thieno[2,3-b][1,5]benzodiazepine | 2.50 |
| Other Ingredients | |
| Mannitol | 234.97 |
| Hydroxypropyl methyl cellulose 3 cps | 12.50 |
| Polysorbate 20 | 0.028 |
| 1b. 750 mg Sachets | |
| Active 2-methyl-4-(4-methyl-1-piperazinyl)-10H-thieno[2,3-b][1,5]benzodiazepine | 7.50 |
| Other Ingredients | |
| Mannitol | 704.93 |
| Hydroxypropyl methyl cellulose 3 cps | 37.49 |
| Polysorbate 20 | 0.08 |
| 1c. 1000 mg Sachets | |
| Active 2-methyl-4-(4-methyl-1-piperazinyl)-10H-thieno[2,3-b][1,5]benzodiazepine | 10.0 |
| Other Ingredients | |
| Mannitol | 939.90 |
| Hydroxypropyl methyl cellulose 3 cps | 49.99 |
| Polysorbate 20 | 0.11 |

Such granules are most preferably contacted with an acidic medium if a suspension or solution is desired.

We claim:

1. A method of treating erectile dysfunction in a mammal comprising administering to the mammal an effective amount of the compound 2-methyl-4-(4-methyl-1-piperazinyl)-10H-thieno[2,3-b][1,5]benzodiazepine, or a pharmaceutically acceptable salt thereof.

2. A method of treating the sexual dysfunction of retarded ejaculation in a mammal comprising administering to the mammal an effective amount of the compound 2-methyl-4-(4-methyl-1-piperazinyl)-10H-thieno[2,3-b][1,5]benzodiazepine, or a pharmaceutically acceptable salt thereof.

3. A method of treating anorgasmy in a mammal comprising administering to the mammal an effective amount of the compound 2-methyl-4-(4-methyl-1-piperazinyl)-10H-thieno[2,3-b][1,5]benzodiazepine, or a pharmaceutically acceptable salt thereof.

4. The method of claim 1 wherein 2-methyl-4-(4-methyl-1-piperazinyl)-10H-thieno[2,3-b][1,5]benzodiazepine is substantially pure Form I 2-methyl-4-(4-methyl-1-piperazinyl)-10H-thieno[2,3-b][1,5]benzodiazepine having an X-ray powder diffraction pattern as follows wherein d represents the interplaner spacing:

d 10.2689
8.577
7.4721
7.125
6.1459
6.071
5.4849
5.2181
5.1251
4.9874
4.7665
4.7158
4.4787
4.3307
4.2294
4.141
3.9873
3.7206
3.5645
3.5366
3.3828
3.2516
3.134
3.0848
3.0638
3.0111
2.8739
2.8102
2.7217
2.6432
2.6007.

5. The method of claim 4 wherein the amount of a compound administered is from about 1 mg to about 20 mg per day.

6. The method of claim 5 wherein the mammal is a human.

7. The method of claim 2 wherein 2-methyl-4-(4-methyl-1-piperazinyl)-10H-thieno[2,3-b][1,5]benzodiazepine is substantially pure Form I 2-methyl-4-(4-methyl-1-piperazinyl)-10H-thieno[2,3-b][1,5]benzodiazepine having an X-ray powder diffraction pattern as follows wherein d represents the interplaner spacing:

d
10.2689
8.577
7.4721
7.125
6.1459
6.071
5.4849
5.2181
5.1251
4.9874
4.7665
4.7158
4.4787
4.3307
4.2294
4.141
3.9873
3.7206
3.5645
3.5366
3.3828
3.2516
3.134
3.0848
3.0638
3.0111
2.8739
2.8102
2.7217
2.6432
2.6007.

8. The method of claim 7 wherein the amount of a compound administered is from about 1 mg to about 20 mg per day.

9. The method of claim 8 wherein the mammal is a human.

10. The method of claim 3 wherein 2-methyl-4-(4-methyl-1-piperazinyl)-10H-thieno[2,3-b][1,5] benzodiazepine is substantially pure Form I 2-methyl-4-(4-methyl-1-piperazinyl)-10H-thieno[2,3-b][1,5] benzodiazepine having an X-ray powder diffraction pattern as follows wherein d represents the interplaner spacing:

d
10.2689
8.577
7.4721
7.125
6.1459
6.071
5.4849
5.2181
5.1251
4.9874
4.7665
4.7158
4.4787
4.3307
4.2294
4.141
3.9873
3.7206
3.5645
3.5366
3.3828
3.2516
3.134
3.0848
3.0638
3.0111
2.8739
2.8102
2.7217
2.6432
2.6007.

11. The method of claim 10 wherein the amount of a compound administered is from about 1 mg to about 20 mg per day.

12. The method of claim 11 wherein the mammal is a human.

* * * * *